(12) United States Patent
Kitagawa

(10) Patent No.: US 7,807,234 B2
(45) Date of Patent: Oct. 5, 2010

(54) PLASMA PROCESSING METHOD, PLASMA PROCESSING APPARATUS, AND COMPUTER RECORDING MEDIUM

(75) Inventor: Junichi Kitagawa, Tokyo (JP)

(73) Assignee: Tokyo Electron Limited, Tokyo (JP)

( * ) Notice: Subject to any disclaimer, the term of this patent is extended or adjusted under 35 U.S.C. 154(b) by 1310 days.

(21) Appl. No.: 11/197,554

(22) Filed: Aug. 5, 2005

(65) Prior Publication Data

US 2005/0287725 A1    Dec. 29, 2005

Related U.S. Application Data

(63) Continuation-in-part of application No. PCT/JP2004/001180, filed on Feb. 5, 2004.

(30) Foreign Application Priority Data

Feb. 6, 2003    (JP)    ............................ 2003-029530

(51) Int. Cl.
   *C23C 16/511*    (2006.01)
(52) U.S. Cl. ...................................... 427/575; 438/778
(58) Field of Classification Search .................. None
   See application file for complete search history.

(56) References Cited

U.S. PATENT DOCUMENTS

| | | | | |
|---|---|---|---|---|
| 6,245,616 B1 * | 6/2001 | Buchanan et al. | ............ | 438/287 |
| 2001/0021592 A1 * | 9/2001 | Lee et al. | ................... | 438/783 |
| 2001/0034107 A1 * | 10/2001 | Fukazawa et al. | ........... | 438/400 |
| 2001/0052323 A1 * | 12/2001 | Yieh et al. | ................... | 118/725 |
| 2002/0025691 A1 * | 2/2002 | Ohmi et al. | ................. | 438/787 |
| 2002/0177270 A1 * | 11/2002 | Beyer et al. | ................. | 438/221 |
| 2003/0224616 A1 | 12/2003 | Ogawa et al. | | |
| 2004/0248392 A1 * | 12/2004 | Narwankar et al. | ......... | 438/584 |

FOREIGN PATENT DOCUMENTS

| | | | |
|---|---|---|---|
| EP | 1347506 A1 | | 9/2003 |
| JP | 2000-294550 | * | 10/2000 |
| JP | 2001-332724 | * | 11/2001 |
| JP | 2002-261097 A | | 9/2002 |
| JP | 2004-47948 A | | 2/2004 |
| JP | 2004-111739 | * | 4/2004 |
| WO | WO03/015151 | * | 2/2003 |

OTHER PUBLICATIONS

Translation of JPP010215 (filed Aug. 2, 2001) by Kazuo Yoshii supplied for U.S. Appl. No. 10/485,410 used as a translation for WO03/015151.*
Gusev, J. App. Phys., V84, 5, p. 2980-2983, 1998.*
Machine Translation of Kawakami (JP2000-294550).*
Machine translation of Masanobu (JP2004-111739).*

* cited by examiner

*Primary Examiner*—Timothy H Meeks
*Assistant Examiner*—Joseph Miller, Jr.
(74) *Attorney, Agent, or Firm*—Oblon, Spivak, McClelland, Maier & Neustadt, L.L.P.

(57) ABSTRACT

According to the present invention, plasma oxidation processing and plasma nitridation processing are applied at the same time to the surface of a semiconductor substrate by plasma using a microwave. After forming an insulating film by the plasma oxynitridation processing as described above, the plasma nitridation processing is further applied to the insulating film as necessary. Thereby, it is possible to form the insulating film with an excellent electrical characteristic.

1 Claim, 13 Drawing Sheets

FIG.5

| PROCESSING | EMBODIMENT 1 | CONVENTIONAL EXAMPLE | COMPARATIVE EXAMPLE 1 | COMPARATIVE EXAMPLE 2 |
|---|---|---|---|---|
| | PLASMA OXYNITRIDATION | THERMAL OXIDATION | PLASMA OXIDATION → PLASMA NITRIDATION | PLASMA OXIDATION |
| TDDB | 1.48 | 1.00 | 0.95 | 1.14 |
| LEAK | 1.01 | 1.00 | 0.31 | 1.07 |
| ELECTRON TRAP (FIG. 4A) | ALMOST THE SAME AS REF | REF (REFERENCE) | MORE | MORE |
| HOLE TRAP (FIG. 4B) | LESS | REF (REFERENCE) | LESS | LESS |

| NO. | | 1 | 2 | 3 | 4 |
|---|---|---|---|---|---|
| BASE | | $SiO_2$ 75 Å | $SiO_2$ 75 Å | $SiO_2$ 75 Å | $SiO_2$ 75 Å |
| ONx | Ar(SCCM) | 500 | 500 | 500 | 500 |
| | $N_2$(SCCM) | 10 | 10 | 10 | 10 |
| | $O_2$(SCCM) | 5 | 2.5 | 1.25 | 0.62 |
| | $H_2$(SCCM) | | | | |
| | PRESS(Pa) | 53.3 | 133.3 | 133.3 | 133.3 |
| | TIME(SEC) | 220 | 220 | 220 | 220 |
| | POWER(W) | 3500 | 3500 | 3500 | 3500 |
| PEAK OF NITROGEN | INT.(V) | 0.87 | 0.95 | 2.05 | 6.85 |
| NITROGEN CONCENTRATION | (atoms/cm$^3$) | 1.74E+21 | 1.91E+21 | 4.09E+21 | 1.37E+22 |
| PARTIAL PRESSURE OF OXYGEN(Pa) | | 0.52 | 0.65 | 0.33 | 0.16 |
| GAS FLOW RATE RATIO $N_2 : O_2$ | | 1:2 | 1:4 | 1:8 | 1:16 |
| PARTIAL PRESSURE OF NITROGEN(Pa) | | 1.03 | 2.6 | 2.6 | 2.6 |

FIG.11

| NO. | | 1 | 2 | 3 | 4 | 5 | 6 | 7 |
|---|---|---|---|---|---|---|---|---|
| BASE | | $SiO_2$ 100 Å | $SiO_2$ 100 Å | $SiO_2$ 100 Å | $SiO_2$ 100 Å | --- | $SiO_2$ 90 Å | Th-SiON |
| ONx | Ar(SCCM) | 500 | 500 | 500 | 500 | 500 | 500 | |
| | $N_2$(SCCM) | 10 | 7.5 | 5 | 2.5 | 5 | 5 | |
| | $O_2$(SCCM) | 5 | 5 | | 5 | 5 | 5 | |
| | $H_2$(SCCM) | | | | | 5 | | |
| | PRESS(Pa) | 133.3 | 133.3 | 133.3 | 133.3 | 133.3 | 133.3 | |
| | TIME(SEC) | 200 | 200 | 200 | 200 | 828 | 600 | |
| | POWER(W) | 3500 | 3500 | 3500 | 3500 | 3500 | 3500 | |
| | INT.(V) | 0.86 | 0.83 | 0.68 | 0.19 | 1.07 | 1.32 | 1.12 |
| PEAK OF NITROGEN NITROGEN CONCENTRATION | (atoms/cm³) | 1.72E+21 | 1.67E+21 | 1.36E+21 | 3.80E+20 | 2.13E+21 | 2.64E+21 | 2.23E+21 |
| PARTIAL PRESSURE OF NITROGEN(Pa) | | 2.59 | 1.95 | 1.31 | 0.66 | 1.29 | | |
| GAS FLOW RATE RATIO $N_2 : O_2$ | | 2:1 | 1.5:1 | 1:1 | 0.5:1 | 1:1 | | |

FIG.13

| NO. | | 1 | 2 | 3 | 4 | 5 | 6 | 7 |
|---|---|---|---|---|---|---|---|---|
| BASE | | SiO₂ 100 Å | SiO₂ 100 Å | SiO₂ 100 Å | SiO₂ 100 Å | SiO₂ 100 Å | SiO₂ 100 Å | SiO₂ 100 Å |
| ONx | Ar(SCCM) | 500 | 500 | 500 | 500 | 500 | 500 | 200 |
| | N₂(SCCM) | 20 | 20 | 20 | 20 | 20 | 20 | 150 |
| | O₂(SCCM) | | | | 5 | | | |
| | H₂(SCCM) | | | | | | | |
| | PRESS(Pa) | 53.3 | 133.3 | 133.3 | 133.3 | 66.65 | 133.3 | 126.635 |
| | TIME(SEC) | 120 | 10 | 30 | 10 | 120 | 10 | 30 |
| | POWER(W) | 3500 | 3500 | 3500 | 3500 | 3500 | 3500 | 1500 |
| | INT.(V) | 9.79 | 6.19 | 10.09 | 3.17 | 8.93 | 5.47 | 2.45 |
| PEAK OF NITROGEN NITROGEN CONCENTRATION | (atoms/cm³) | 1.96E+22 | 1.24E+22 | 2.02E+22 | 6.34E+21 | 1.79E+22 | 1.09E+22 | 4.90E+21 |

PLASMA PROCESSING METHOD, PLASMA PROCESSING APPARATUS, AND COMPUTER RECORDING MEDIUM

This is a continuation in part of PCT Application No. PCT/JP2004/001180, filed Feb. 5, 2004, which claims the benefit of a Japanese Patent Application No. 2003-029530, filed Feb. 6, 2003, all of which are incorporated herein by reference.

BACKGROUND OF THE INVENTION

1. Field of the Invention

The present invention relates to a plasma processing method forming an insulating film on the surface of a substrate by using plasma, a plasma processing apparatus for performing the plasma processing method, and a computer recording medium.

2. Description of the Related Art

As an insulating film formed on a silicon substrate, a thermal oxide film formed by performing oxidation processing at high temperature of 1000° C. or higher has been often used conventionally. As microfabrication technology advances in recent years, it becomes necessary to reduce the thickness of this kind of oxide film (insulating film) in which reaction of Si and O progresses only by thermal energy.

However, according to the formation method of the insulating film by thermal oxidation processing at high temperature, a leakage current and the like increase as the thickness decreases and it is difficult to obtain the insulating film with high reliability. Further, a nonvolatile memory which performs reading and writing by passing a current through the insulating film has the problem of deterioration in its memory characteristic due to holes or electrons trapped in the insulating film. It is considered that the hole traps particularly affect reliability of a product.

In order to solve the above problem, oxidation processing by active atomic oxygen (hereinafter referred to as the "oxygen radical") using plasma, whose reaction mechanism is different from that of the thermal oxidation method, has been realized. According to this method, it is possible to form the oxide film while electron temperature of the plasma is kept at low temperature, which results in reducing damages to the substrate to be processed and an inner wall of a processing apparatus. Further, since the hole traps are reduced, it becomes possible to form the thin oxide film without affecting the reliability.

Japanese Patent Application No. Tokukai-Hei 11-293470 discloses the formation method of the oxide film using the plasma. This is a method of forming a silicon oxide film by introducing a silicon-containing gas and an oxygen-containing gas into a process chamber, and generating plasma of these gases, to deposit the silicon oxide film on the substrate. Besides the aforesaid silicon-containing gas and the oxygen-containing gas, a hydrogen gas is introduced into the process chamber to generate the plasma containing hydrogen in the process chamber. Thereby, it is possible to obtain the excellent film quality equivalent to the thermal oxide film.

SUMMARY OF THE INVENTION

However, the oxide film (insulating film) formed on the surface of the substrate using the plasma has a worse electron trap characteristic than the oxide film formed by the oxidation processing at high temperature. Hence, it is considered that it is weak in electrical stress and its characteristic as a product (e.g. semiconductor device) deteriorates.

Meanwhile, thermal nitridation is sometimes performed after the thermal oxidation in order to improve various characteristics of the thermal oxide film. It is considered that the various characteristic are improved because the nitridation compensates defective binding of Si—O which is generated during the thermal oxidation. However, according to the thermal nitridation method, nitrogen distribution in the direction of the depth deviates to a substrate interface part, and hence it is not good enough to improve the oxide film uniformly. Therefore, in order to improve the characteristic of the plasma oxidation film which is weak in the electrical stress, the method of performing nitridation processing after plasma oxidation processing, similarly to a thermal oxide nitride film, has been studied.

DISCLOSURE OF THE INVENTION

The present invention is made in view of the circumstances described above, and it is an object of the present invention to provide a method of forming an insulating film (silicon oxynitride film, for example) with an excellent electrical characteristic, a plasma processing apparatus, and a computer recording medium.

In order to achieve the above object, a plasma processing method according to the present invention applies plasma oxidation processing and plasma nitridation processing at the same time to a surface of a semiconductor substrate. Thereby, a trap characteristic of the formed insulating film is improved. Incidentally, performing the oxidation and the nitridation at the same time means that at least main processing periods during which the respective processing is stably performed are the same, and the beginnings and the ends of the respective processing may be temporally different.

It is preferable that electron density of the plasma is $1.0 \times 10^{12}$ ($1/cm^3$) or more and electron temperature of the plasma is 1.0 (eV) or less. it is possible for a plasma source using a microwave to easily generate the plasma having the electron density and the electron temperature of these values. Additionally, an uniform plasma region (i.e. uniform quality plasma) can be formed by the plasma using the microwave, and hence it is suitable to form the oxynitride film as in the present invention.

It is suitable to further apply the plasma nitridation processing to the insulating film, after forming the insulating film by the plasma oxynitridation processing as described above. Thereby, it is possible to control the distribution of the nitrogen in the direction of the depth, which has been difficult according to the thermal nitridation or thermal oxynitridation processing. Further, in the oxidation and the nitridation performed at the same time, it is possible to control the nitrogen distribution by controlling a mixing ratio of an oxygen gas.

By changing the mixing ratio, that is, a flow rate ratio of the oxygen to the nitrogen gas, a peak of nitrogen concentration in the insulating film can be changed. Hence, in this case, it is unnecessary to apply the plasma nitridation processing after forming the insulating film as described above. According to knowledge of the present inventor, when the flow rate ratio of the oxygen to the nitrogen gas is preferably set to 1:4 to 1:6 range, peaks of the nitrogen concentration can be formed on a side of an interface with the substrate and a side of a surface of the insulating film, respectively, as will be described later.

According to another aspect of the present invention, the nitrogen diffuses in the direction of the thickness from the surface of the insulating film to the interface with the substrate, and the nitrogen distribution has its peak at the position closer to the interface than the surface of the insulating film. Alternatively, the nitrogen distribution has two peaks which are near the surface of the insulating film and near the interface. Thus, it is possible to obtain the semiconductor substrate having the insulating film formed by the plasma, whose trap characteristic is improved. Thus-structured semiconductor substrate avoids unnecessary reoxidation in its post-process, and poses a barrier to injected impurities. Thus, the semiconductor substrate having the stable insulating film which is hardly affected by conditions of semiconductor fabrication process can be obtained.

According to another aspect of the present invention, a plasma processing apparatus applying plasma processing to a substrate, comprises a process vessel containing the semiconductor substrate, a microwave introducing portion introducing a microwave to the process vessel, and a gas supply portion supplying process gases to the process vessel, wherein the oxygen and the nitrogen are supplied at the same time by the gas supply portion into the process vessel, and oxidation processing and oxidation processing are applied at the same time to a surface of the semiconductor substrate to form an insulating film.

In this case, the gas supply portion may be structured so as to supply the nitrogen into the process vessel to further apply the nitridation processing to the insulating film after the oxidation and the nitridation processing of the semiconductor substrate.

According to the plasma processing apparatus structured as above, it is possible to perform the aforesaid plasma processing method suitably, and to fabricate the excellent semiconductor device.

BRIEF DESCRIPTION OF THE DRAWINGS

FIG. 5 is a chart showing a secular change characteristic until dielectric breakdown;

FIG. 11 is a table showing the change of the peak of the nitrogen concentration in the insulating film when the flow rate and processing time of a nitrogen gas are changed;

FIG. 13 is a table showing the change of the peak of the nitrogen concentration in the insulating film when the processing time and a processing pressure are changed.

DETAILED DESCRIPTION OF THE INVENTION

Figure 1:
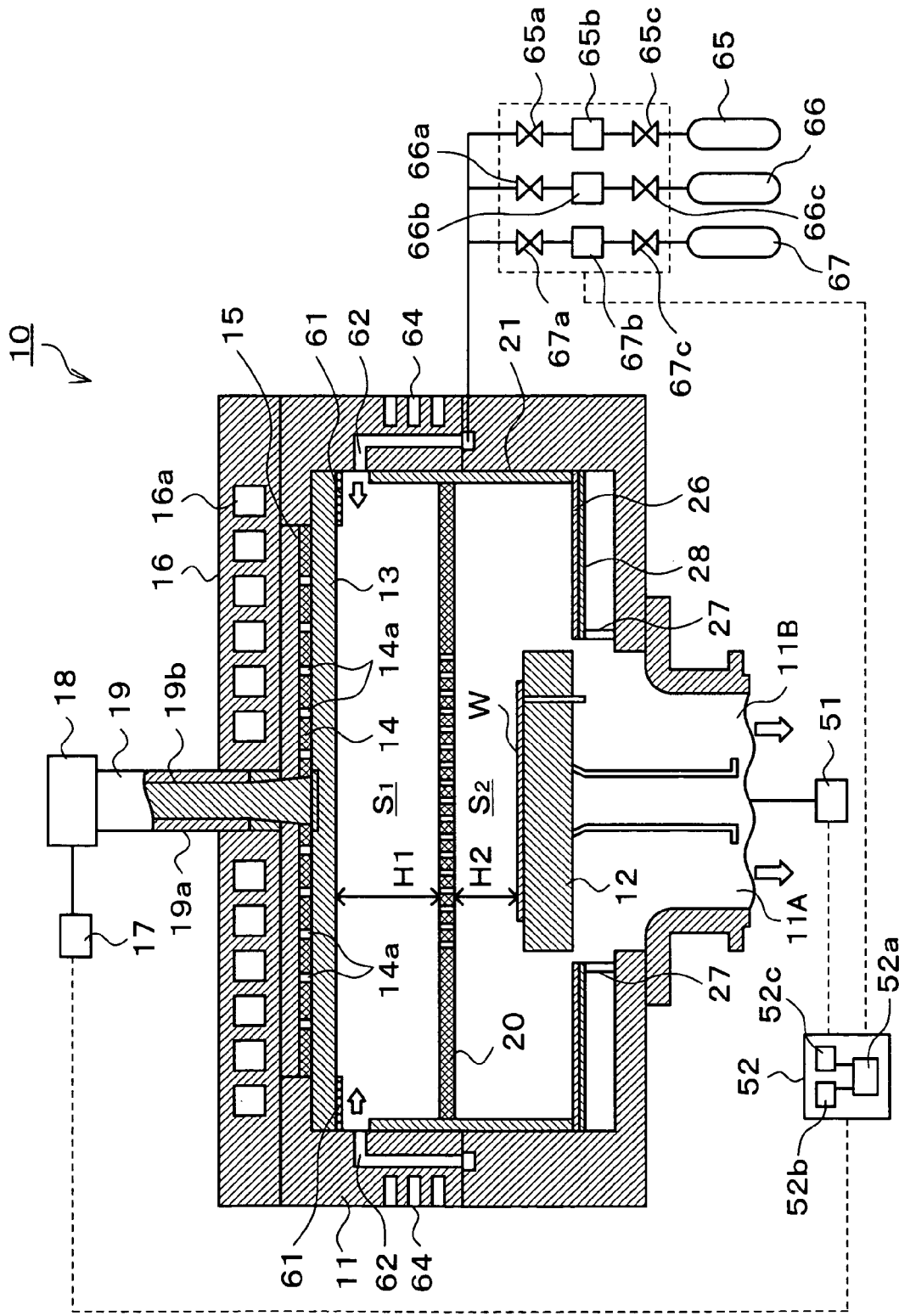
FIG. 1 is a schematic view (sectional view) showing an example of the structure of a plasma processing apparatus according to an embodiment of the present invention.

FIG. 1 shows a schematic structure of a plasma processing apparatus 10 according to an embodiment of the present invention. The plasma processing apparatus 10 has a process vessel 11 in which a substrate holding table 12 for holding a silicon wafer W as a substrate is formed, and air (gas) inside the process vessel 11 is exhausted by an exhaust device 51 through exhaust ports 11A and 11B. Note that the substrate holding table 12 has a heater function for heating the silicon wafer W (a heater itself is not shown).

The process vessel 11 has an opening formed in an upper portion at a position corresponding to the silicon wafer W on the substrate holding table 12. This opening is closed by a dielectric plate 13 made of quartz, $Al_2O_3$, AlN, or the like. In this embodiment, quartz is used for the dielectric plate 13. The dielectric plate 13 is supported by a support portion 61 projected toward the inside of the vessel 11. On (on an outer side of) the dielectric plate 13, a slot plate 14 composed of a planar antenna to function as an antenna is provided. The slot plate 14 is made of a plate (like a thin disk) of a conductive material, for example, copper or aluminum plated with silver or gold, and has a large number of slits 14a. The disk may have rectangle shape or polygon shape. These slits 14a are arranged spirally or coaxially as a whole.

On (on an outer side of) the slot plate 14, disposed is a dielectric plate 15 made of, for example, quartz, alumina, aluminum nitride, or the like. This dielectric plate 15 is sometimes called a retardation plate or a wavelength shortening plate. In this embodiment, quartz is used for the dielectric plate 15. On (on an outer side of) the dielectric plate 15, a cooling plate 16 is disposed. The cooling plate 16 has therein a refrigerant path 16a in which a refrigerant flows. Cooling a microwave introducing portion prevents the dielectric plate 13, the slot plate 14, the dielectric plate 15 and the like from being broken by heat, and makes a contribution to maintain stability of plasma. Further, a rectangular waveguide 18 and a coaxial waveguide 19 which introduce a microwave of, for example, 2.45 GHz generated by a microwave supply device 17 are provided in an upper edge center of the process vessel 11. The coaxial waveguide 19 is composed of an outer conductor 19a and an inner conductor 19b. In this embodiment, these dielectric plate 13 and slot plate 14 constitute a plasma generating part. The aforesaid microwave is introduced into the process vessel 11 through the slot plate 14 and the dielectric plate 13 to generate the plasma.

Around the substrate holding table 12, a gas baffle plate 28 made of aluminum is disposed. On an upper face of the gas baffle plate 28, a quartz cover 26 is provided. The gas baffle plate 28 is supported by a support portion 27.

On the inner wall of the process vessel 11, a gas nozzle 22 as a gas introducing part for introducing gas is provided. In this embodiment, an inert gas supply source 65, a nitrogen gas supply source 66, and an oxygen gas supply source 67 are prepared as gas supply sources, and they are connected to the gas nozzle 22 via valves 65a, 66a, 67a, mass flow controllers 65b, 66b, 67b, and valves 65c, 66c, 67c, respectively.

A flow rate of gas supplied from the gas nozzle 22 is controlled by the mass flow controllers 65b, 66b, 67b. In the sidewalls of the process vessel 11, a refrigerant path 24 is formed to surround the entire vessel.

A controller 52 controls ON-OFF and output control of the aforesaid microwave supply device 17, the flow rate adjustment by the mass flow controllers 65b, 66b, 67b, the adjustment of an exhaust amount of the exhaust device 51, the heater function of the substrate holding table 12, and the like, so as to allow the plasma processing apparatus 10 to perform optimum processing.

This controller 52 controls the plasma processing apparatus 10. The controller 52 has a central processing unit 52a, a support circuit 52b, and a storage medium 52c in which relevant control software is contained. A processor of a general-purpose computer may be used as the central processing unit 52a of the controller 52. Various types of the storage medium, such as a RAM, ROM, flexible disk, hard disk, for example, may be used as the storage medium 52c. The support circuit 52b is connected to the central processing unit 52a to support the processor in various ways.

The storage medium 52c stores various control programs which are necessary for thus-structured plasma processing apparatus 10 according to the present invention to carry out a plasma processing method, and other software are stored.

An example to work the present invention using the plasma processing apparatus 10 is as follows. First, the silicon wafer W as a semiconductor substrate is set in the process vessel 11 of the plasma processing apparatus 10 and then the air inside the process vessel 11 is exhausted through the exhaust ports 11A and 11B so that the inside of the process vessel 11 is set to a predetermined process pressure. Thereafter, an inert gas, an oxygen gas, and a nitrogen gas are mixed in advance and introduced from the gas nozzle 62 into the process vessel 11 in which the silicon wafer W is set. It is suitable to provide a plurality of the gas nozzles 62 and separately introduce the respective gases to the process vessel 11 through the respective nozzles. Alternatively, it is also suitable to bring a plurality of pipes for the respective gases together near the gas nozzle 62 and introduce the gases while mixing them near the nozzle. Whichever the case may be, the gases may be supplied in any way as long as they exist at the same time in the same plasma processing.

Meanwhile, the microwave with the frequency of 2.45 GHz supplied through the rectangular waveguide 18 and the coaxial waveguide 19 is introduced into the process vessel 11 through the dielectric plate 15, the slot plate 14, and the dielectric plate 13. This microwave excites the plasma, and oxygen radicals and nitrogen radicals are generated from the mixed gas of the inert gas, the oxygen, and the nitrogen.

It is preferable that electron density of the plasma at this time is $1.0 \times 10_{12}$ ($1/cm^3$) or more, and electron temperature thereof is 1.0 (eV) or less. Thereby, it is possible to reduce damage to an oxynitride film to be formed.

In this regard, for example, another plasma source for generating high density plasma, an ECR plasma, for example, has the high possibility of giving plasma damage to the substrate. Namely, there is the possibility that the substrate stores unnecessary charge or a formed bond of Si—N—O is broken and hence, it is impossible to form the fine oxynitride film.

Therefore, when the processing is performed by the plasma with high density and low electron temperature using the microwave as in this embodiment, there is no such possibility that the substrate stores the unnecessary charge or the formed bond of Si—N—O is broken and hence, it is possible to form the fine oxynitride film.

Because the plasma has the high density and the low electron temperature, it is possible to dispose the silicon wafer W close to the plasma, and suppress a drop of a film formation rate.

Namely, since the conventional plasma source, for example, the ECR plasma has high energy, it is necessary to dispose the silicon wafer W comparatively separately from a plasma region. In this case, there is the high possibility that lives of the generated oxygen radicals end before they reach the silicon wafer W (what is called "deactivation"), thereby dropping the film formation rate.

However, according to this embodiment, the silicon wafer W can be disposed close to the plasma because the processing is performed by the plasma using the microwave. As a result of this, a large number of the oxygen radicals can reach the silicon wafer W before the lives of the oxygen radicals end. Thus, it is possible to suppress the drop of the film formation rate and to form the excellent oxide film and oxynitride film.

Figure 2A:
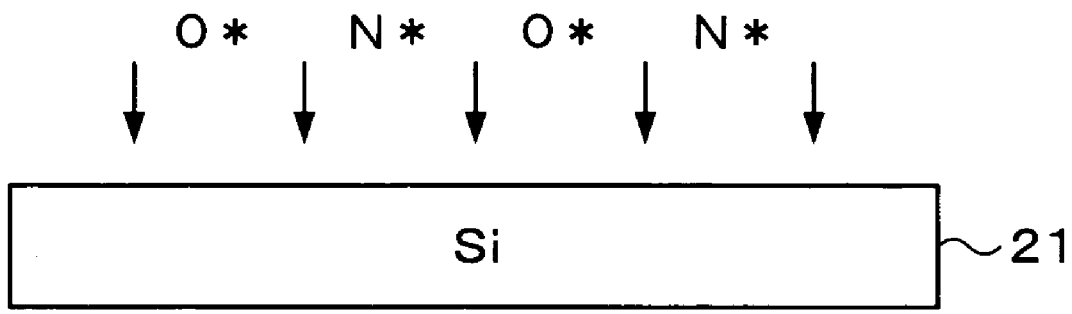
FIG. 2A and FIG. 2B are schematic views showing a part of the flow of plasma processing according to an embodiment 1.
Figure 2B:

The oxygen radicals and the nitrogen radicals reaching the surface of a silicon substrate 21 subject the surface of the silicon substrate 21 to oxidation and nitridation processing as shown in FIG. 2B, to form a silicon oxynitride film 22 having a desired thickness (10 nm or less, for example). Thus, a semiconductor substrate having an insulating film formed by performing the oxidation and the nitridation at the same time (embodiment 1) is obtained.

Figure 4A:
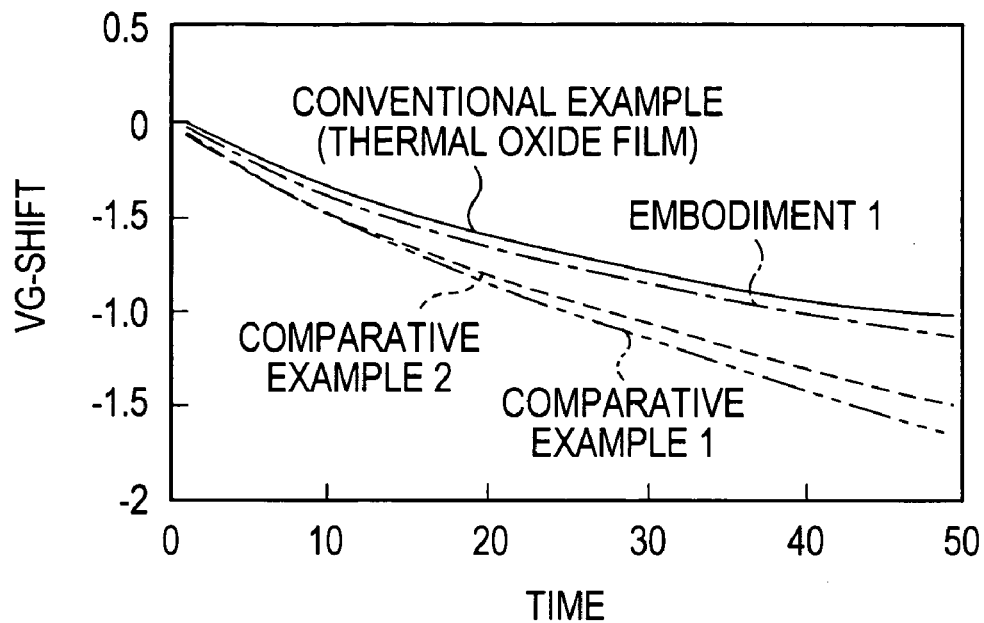
FIG. 4A and FIG. 4B are graphs showing the trap characteristics of various insulating films.
Figure 4B:
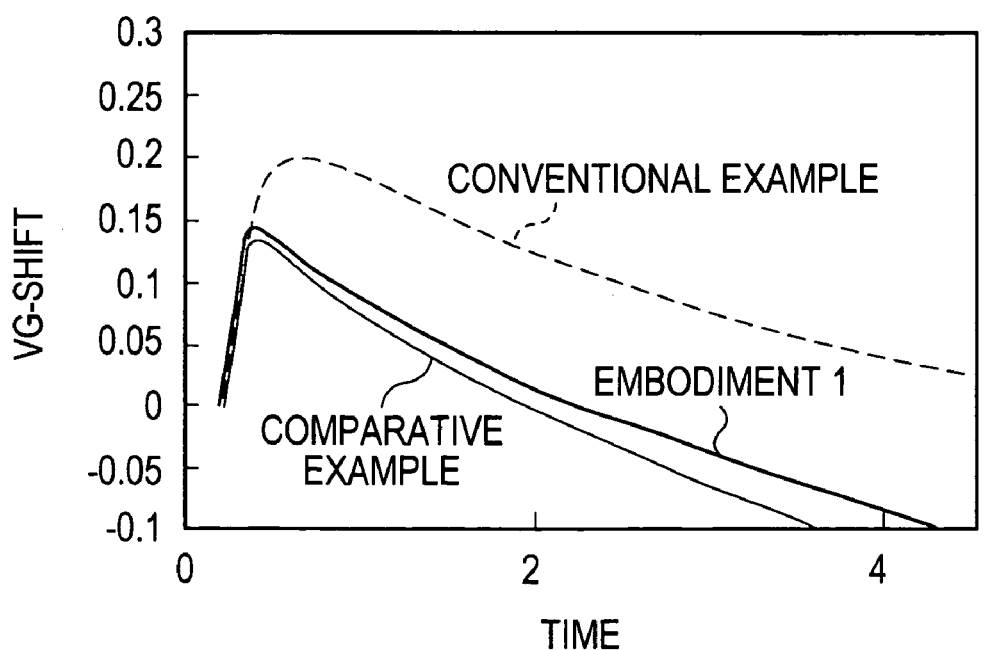

Meanwhile, a semiconductor substrate having a thermal oxide film (conventional example); a semiconductor substrate having an insulating film which is subjected to plasma nitridation after plasma oxidation (comparative example 1); and a semiconductor substrate having a plasma oxidation film only (comparative example 2) are prepared for comparison purposes. Then, trap characteristics thereof, together with the aforesaid embodiment 1, are measured and compared for evaluation. The results are shown in FIGS. 4A, and 4B.

Figure 3A:
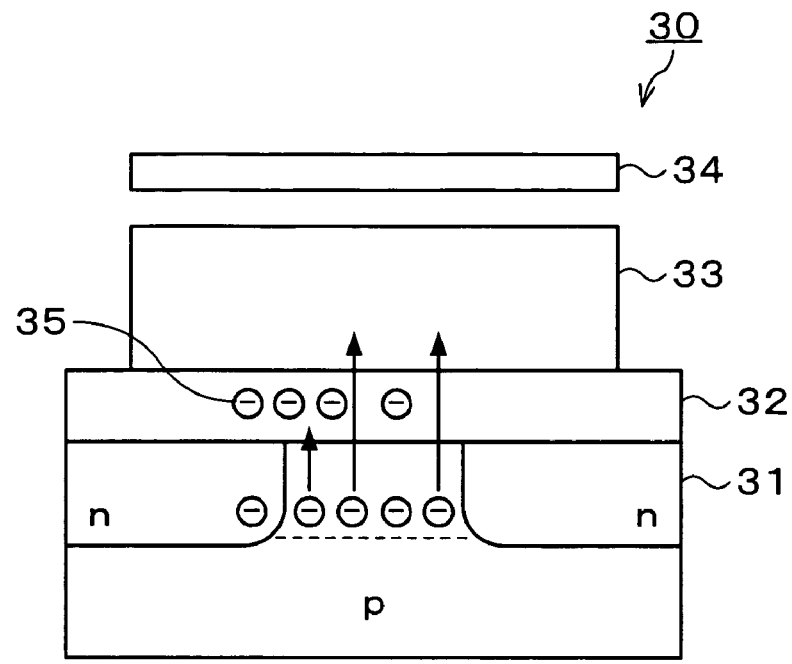
FIG. 3A is a view explaining a trap characteristic and FIG. 3B is a view showing the outline of how to measure the trap characteristic as an example.

The mechanism of the trap of electrons is exemplified in FIG. 3A. For example, in rewriting a flash memory 30, the electrons are drawn from a semiconductor substrate 31 through an insulating film (oxide film) 32 to a floating gate 33. At this time, when film quality of the insulating film 32 is poor, a large number of the electrons 35 stay inside the insulating film, and the electrons ($e^-$) passing therethrough are gradually reduced in number. This phenomenon is called the trap. In this example, after the flash memory 30 is rewritten, a writing characteristic of the memory deteriorates due to the trapped electrons 35.

Figure 3B:
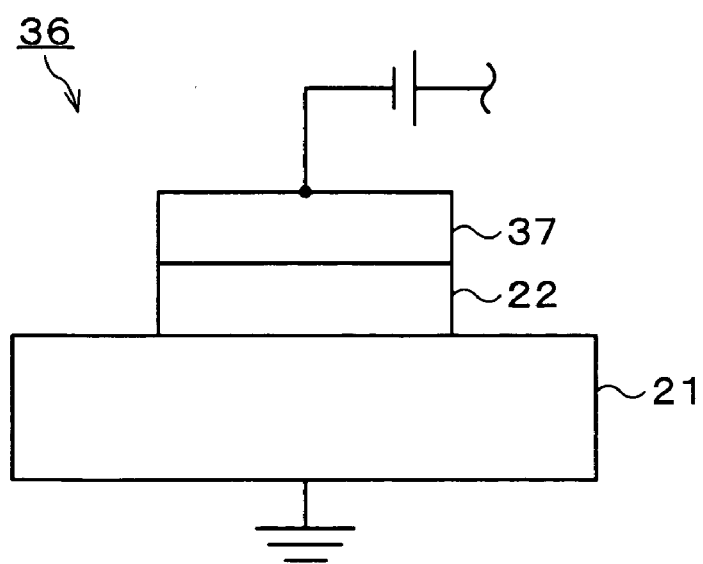

The trap characteristic is measured by making the semiconductor substrate a MOS capacitor 36 as shown in FIG. 3B, for example. This MOS capacitor is formed by providing the insulating film (oxide film) 22 on the silicon substrate 21 formed as above, and providing an electrode 37 thereon for passing a certain current. The trap characteristic is measured by measuring a potential difference between the electrode 37 and the semiconductor substrate 21.

When an N-MOS capacitor is used, negative voltage is applied to the electrode 37 to measure secular change of the voltage. In general, measured data is roughly classified into FIGS. 4A and 4B. At an early stage of the measurement (FIG. 4B), hole traps are observable, and from the subsequent measurement (FIG. 4A), electron traps are observable. An initial voltage value which is applied between the semiconductor substrate and the electrode gradually shifts toward the negative side over time. The larger the voltage value shifts, the more the electrons are trapped and the lower the possibility that the electrons pass through the insulating film. In applying this to the flash memory as described above, the more the electrons are trapped in writing, the lower the possibility that the electrons pass therethrough. Therefore, it is hard to perform writing and as a result, its writing characteristic appears to be deteriorated.

FIGS. 4A and 4B show thus-measured trap characteristic of the electrons by showing relationship of a deviation from the initial voltage value. The horizontal axis denotes standardized time, and the vertical axis denotes the deviation from the initial voltage value (Vg-shift). This deviation is a difference between the applied initial voltage value and a measurement voltage between both ends of the insulating film which changes over time. Therefore, the increase of the electron traps means the shift toward the negative side.

The solid line shows the thermal oxide film of the conventional example, and a chain line shows the semiconductor substrate having the plasma oxynitride film (insulating film) which is formed by performing the plasma oxidation and the plasma nitridation at the same time according to the embodiment 1 of the present invention. Further, the chain double-dashed line shows the semiconductor substrate having the insulating film which is formed by performing the plasma nitridation after the plasma oxidation according to the comparative example 1, and the broken line (dotted line) shows the semiconductor substrate having the plasma oxide film according to the comparative example 2, respectively. As is clear from the graphs, the embodiment 1 has the excellent characteristic which is almost the same as that of the conventional thermal oxide film, whereas both of the comparative examples have a large number of the electron traps and their performance as the insulating film is not enough.

Meanwhile, FIG. 5 is a chart showing a secular change characteristic until dielectric breakdown (TDDB: Time Dependent Dielectric Breakdown) when the charge is applied and the current is passed, and a leakage current of the respective samples described above, for the purpose of comparing general electrical characteristics thereof. In this case, relative evaluation is made with reference to values of the thermal oxide film. Note that qualitative representation of the trap characteristics shown in FIGS. 4A and 4B is added to this chart in order to grasp the characteristics of the insulating films more comprehensively.

As is clear from the result, the insulating film obtained by the plasma oxynitridation according to the present invention shows the characteristics which are relatively equal to or greater than those of the conventional thermal oxide film in terms of the leakage current, the electron traps and the hole traps. As to the TDDB in particular, its result is superior to the conventional example. It is considered that the hole trap is the dominant factor of the life of the insulating film (TDDB), and the insulating film is excellent as the number of the hole traps and the electron traps is smaller.

Next, another example to work the present invention using the plasma processing apparatus 10 is shown as follows.

The semiconductor substrate obtained as the embodiment 1 described above is continuously set in the process vessel 11 without being removed from the process vessel 11. The gasses and the like which are used in the embodiment 1 are exhausted from the process vessel 11 through the exhaust ports 11A and 11B. Thereafter, the inert gas and the nitrogen gas which are mixed in advance are introduced through the gas nozzle 62 into the process vessel 11.

Meanwhile, the microwave with the frequency of 2.45 GHz supplied through the rectangular waveguide 18 and the coaxial waveguide 19 is introduced into the process vessel 11 through the dielectric plate 15, the slot plate antenna 14, and the dielectric plate 13. This microwave excites the mixed gas of the inert gas and the nitrogen gas into a plasma state to generate the nitrogen radicals.

Figure 6A:
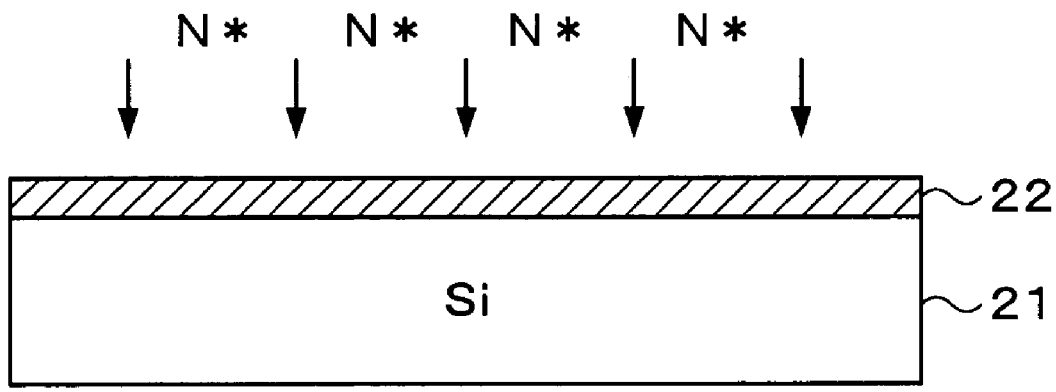
FIG. 6A and FIG. 6B are schematic views showing a part of the flow of plasma processing according to an embodiment 2.
Figure 6B:

The nitrogen radicals reaching the surface of the semiconductor substrate subject the insulating film 22 which is on the surface of the semiconductor substrate to the further nitridation processing, to form a silicon oxynitride film 22A having a desired thickness (10 nm or less, for example), as shown in FIG. 6B. Thus, a semiconductor substrate having the insulating film 22A formed by performing the further nitridation processing after the oxidation and the nitridation are performed at the same time (embodiment 2) is obtained.

Figure 7:
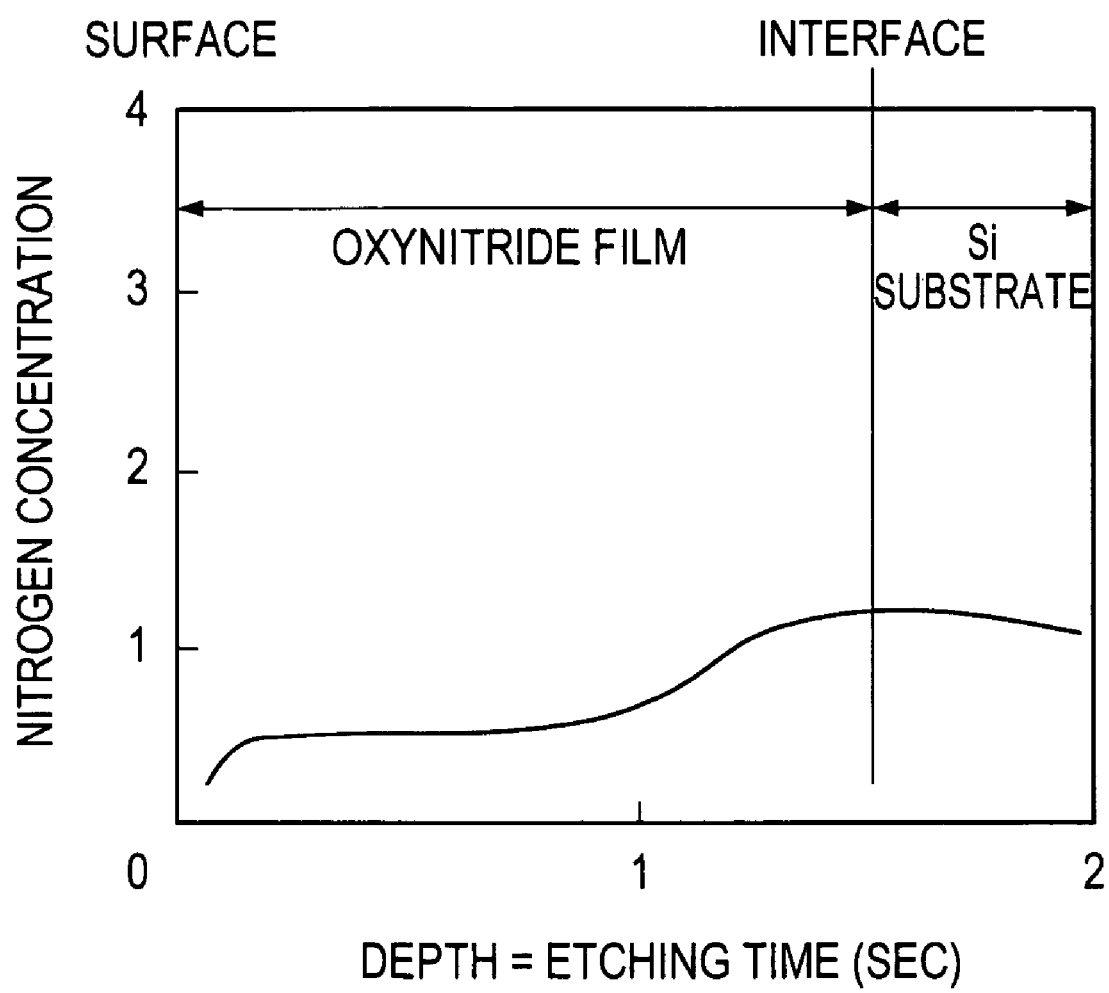
FIG. 7 is a graph showing distribution of nitrogen concentration in the insulating film according to the embodiment 1 of the present invention.

FIG. 7 shows distribution of the nitrogen in the direction of the thickness of the insulating film of thus-obtained semiconductor substrate according to the present invention. In FIG. 7, the horizontal axis denotes etching time. It is shown that it corresponds to the distance in the direction of the thickness of the insulating film, and more etching is applied as time passes to increase the distance and depth from the surface of the insulating film. The vertical axis denotes relative spectral intensity of the nitrogen, and it shows that a large quantity of the nitrogen distributes and exists as the intensity increases.

FIG. 7 shows the nitrogen distribution of the embodiment 1. The nitrogen distributes in the direction of the thickness at least from the surface of the insulating film to an interface with the semiconductor substrate, and the nitrogen distribution has its peak at the position closer to the interface than the surface. Thus, it is possible to obtain the semiconductor substrate having the insulating film with the excellent trap characteristic.

Figure 8:
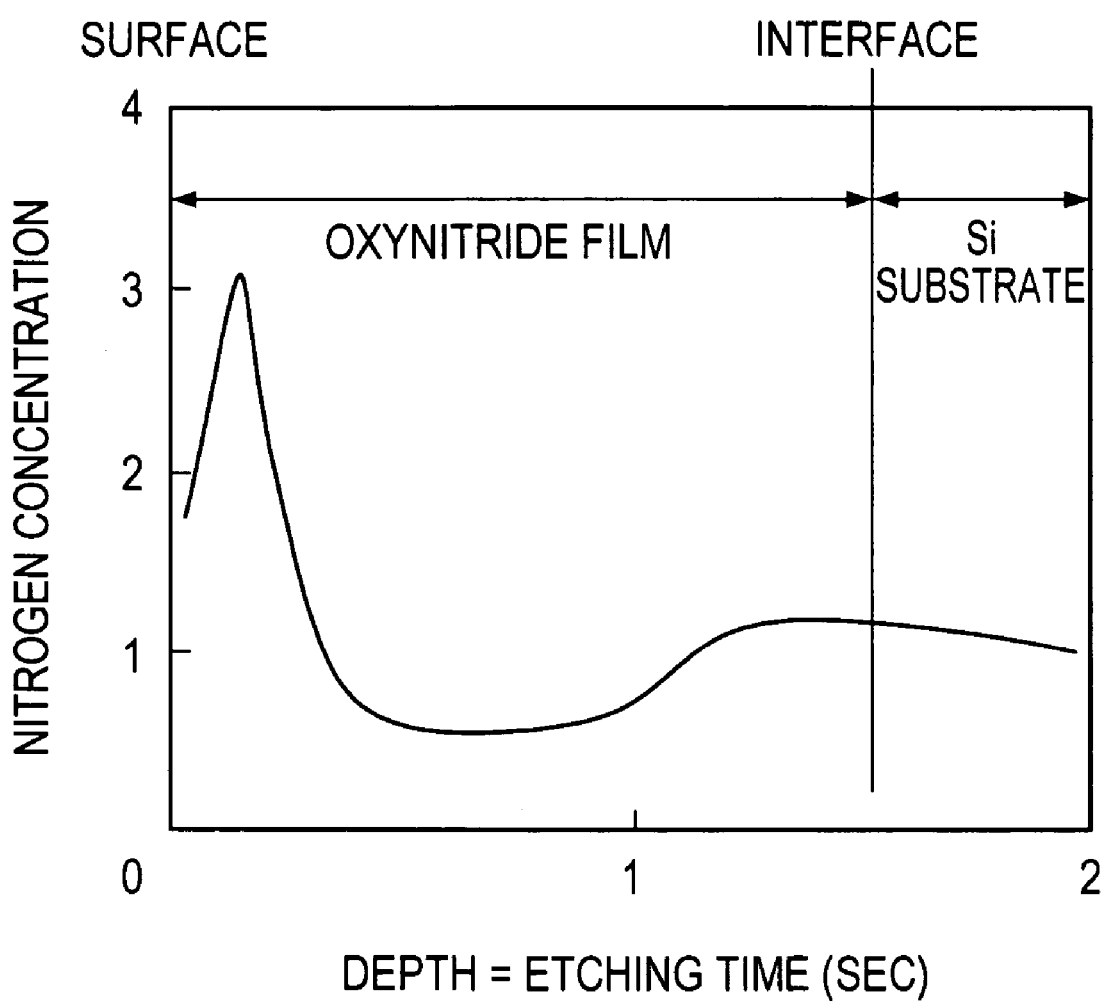
FIG. 8 is a graph showing the distribution of the nitrogen concentration in the insulating film according to the embodiment 2 of the present invention.

FIG. 8 shows the nitrogen distribution of the semiconductor substrate according to the embodiment 2, and it is confirmed that the nitrogen distribution in the insulating film has two peaks which are near the surface and near the interface. Thereby, it is possible to improve the trap characteristic of the insulating film formed by the plasma, avoid reoxidation in its post-process, and pose a barrier to injected impurities. Thus, the semiconductor substrate having the stable insulating film which is hardly affected by conditions of semiconductor fabrication process can be obtained.

According to the embodiment 2, the peak positions of the nitrogen distribution can be changed by setting process conditions appropriately. Thus, it is possible to control the nitrogen distribution in the direction of the thickness of the insulating film, which has been difficult to control in the conventional oxynitridation processing at high temperature.

Next, it is possible to form the insulating film having the two peaks of the nitrogen distribution in the insulating film, which are near the surface and near the interface as shown in FIG. 8, without performing the further nitridation processing after the oxidation and the nitridation are performed at the same time, as in the embodiment 2.

Namely, the oxygen and the inert gas are first made into plasma in the process vessel 11 to form the oxide film on the silicon wafer W. Next, the inert gas and the mixed gas of the oxygen and the nitrogen gas are introduced into the process vessel 11 and made into plasma. Then, the silicon wafer W is subjected to the oxynitridation processing to form the oxynitride film. When the insulating film having the thickness of 8 nm is formed, for example, it is supposed that the thickness of the oxide film is 6 nm and the thickness of the oxynitride film is 2 nm. At this time, a flow rate ratio of the mixed gas of the oxygen to the nitrogen gas is set to be approximately 1:4 to 1:6.

Then, it is possible to form the insulating film having the two peaks of the nitrogen distribution in the insulating film, which are near the surface and near the interface.

Figures 9, 10:
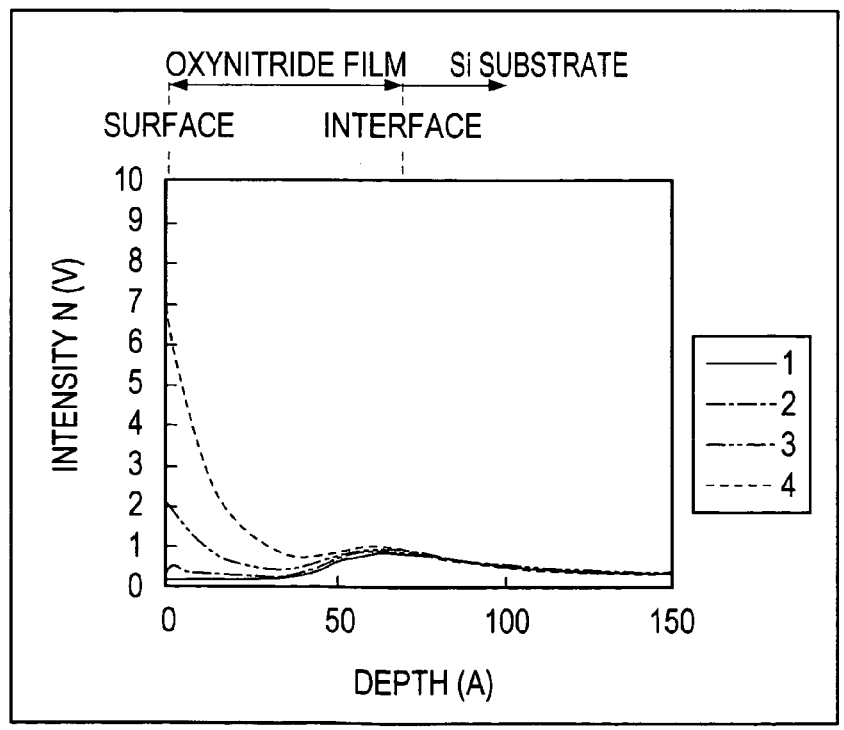
FIG. 9 is a table showing the change of a peak of the nitrogen concentration in the insulating film when a flow rate of an oxygen gas is changed, according to another embodiment of the present invention.
FIG. 10 is a graph showing peak distribution of the nitrogen concentration based on the result of FIG. 9.

Moreover, an explanation is made based on an experiment in FIG. 9 made by the present inventors. FIG. 9 shows the result of the experiment of a peak value of the nitrogen concentration when the nitrogen gas and an argon gas as the inert gas are fixed and a flow rate of the oxygen gas is changed. FIG. 10 is a graph showing depth in the direction of the thickness of the insulating film (the surface of the insulating film) and intensity of the nitrogen concentration, based on FIG. 9. Incidentally, processing conditions are as shown in the table of FIG. 9, and the peak value of the nitrogen concentration (atoms/cm$^3$) is a reduced value from GDS.

As is clear from the result, there are two peaks of the nitrogen concentration which are near the interface of the insulating film and its surface. From these results, a partial pressure of the oxygen gas is preferably 0.4 or less, and more preferably 0.35 or less. Further, the flow rate ratio of $N_2:O_2$ is preferably 1:4 to 1:16, and more preferably 1:5 to 1:10.

Binding energy of Si—O and Si—N is 106 kcal/mol (4.6 eV) and 80 kcal/mol (3.5 eV), respectively, and the binding energy of Si—O is larger. Hence, when the partial pressure of the oxygen is made lower than the partial pressure of the nitrogen, reaction of Si—O precedes and takes the lead although N reacts at the same time in some degree. When the insulating film (SiON) having a certain film thickness is formed as the reaction progresses further, the reaction of Si—O does not progress further and N is dosed to the surface side. Therefore, by controlling the flow rate of $N_2$ and $O_2$, it is possible to realize such a characteristic that the two peaks of the nitrogen concentration appear near the interface of the insulating film and near the surface thereof.

Figure 12:
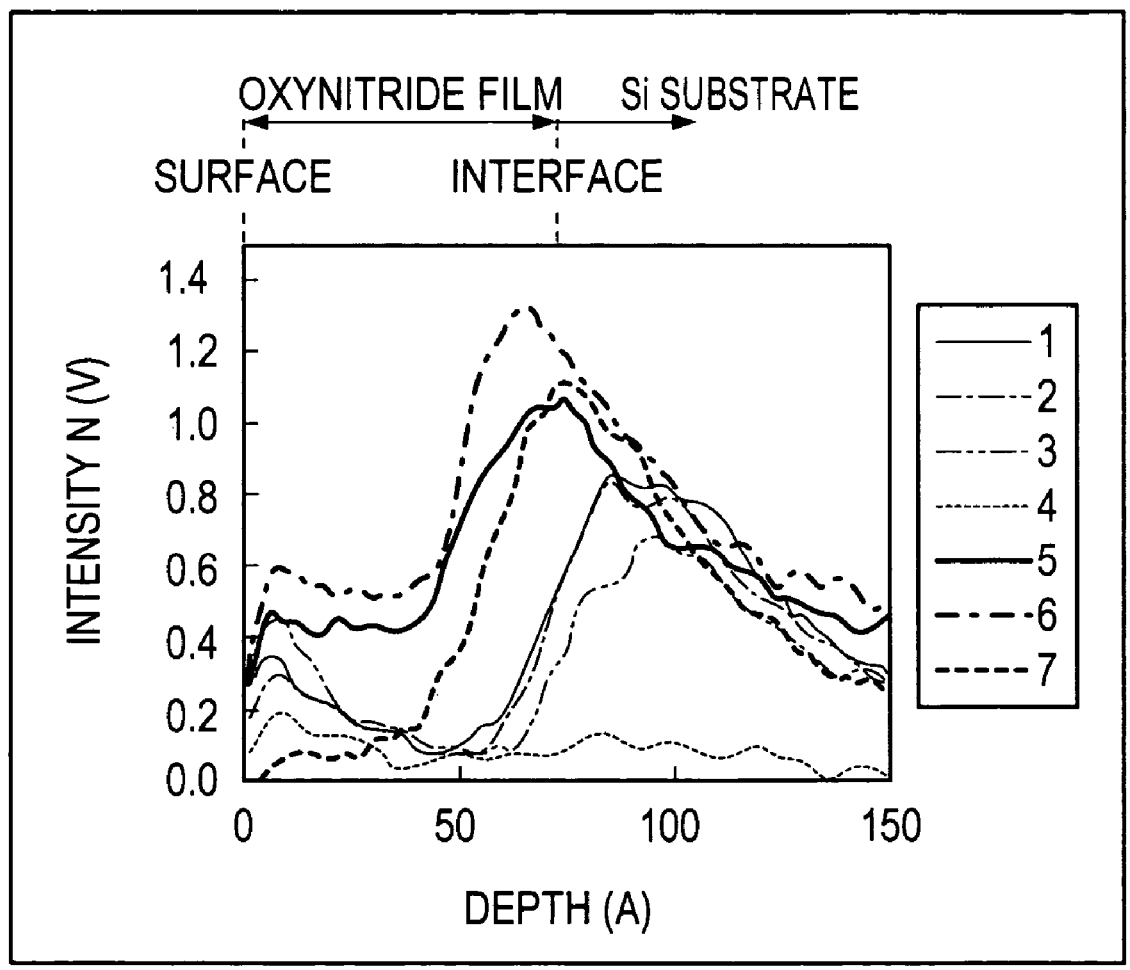
FIG. 12 is a graph showing the peak distribution of the nitrogen concentration based on the result of FIG. 11.

FIG. 11 is a table showing experimental data for optimally controlling the nitrogen distribution on the interface side, and showing the change of the nitrogen concentration peak in the insulating film when the flow rate and the processing time of the nitrogen gas are changed separately. FIG. 12 shows the peak distribution of the nitrogen concentration based on the results of FIG. 11. Note that, in FIG. 11 and FIG. 12, No. 7 is the case of a thermal SiON film. As is clear from the results, it is possible for this embodiment to realize the nitrogen concentration which is equivalent to the thermal SiON film by the plasma processing at low temperature. In this case, it is preferable that the partial pressure of the nitrogen gas is higher than 1 Pa, and the ratio of the flow rate of the nitrogen gas to the flow rate of the oxygen gas is 0.7:1 to 1:2.

Figure 14:
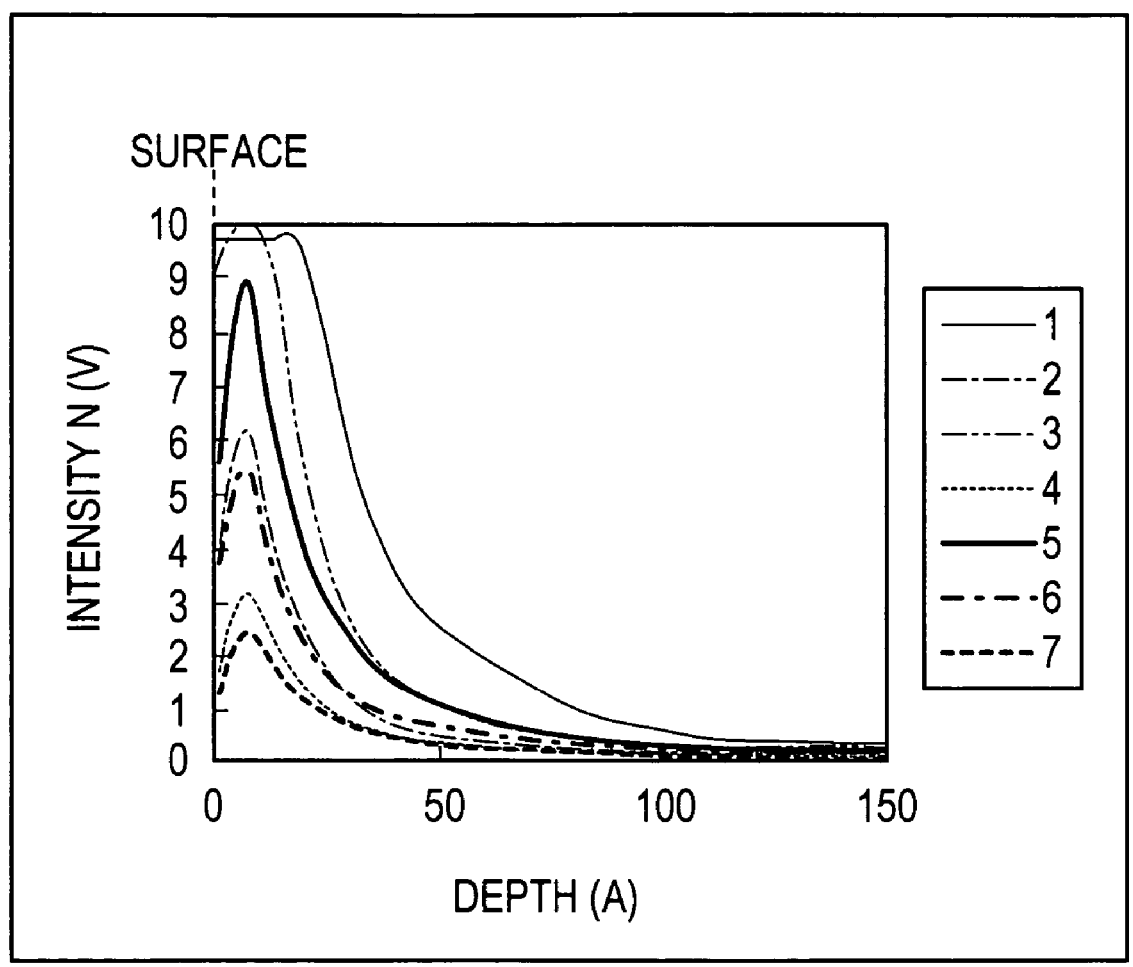
FIG. 14 is a graph showing the peak distribution of the nitrogen concentration based on the result of FIG. 13.

FIG. 13 is a table showing the change of the nitrogen concentration peak in the insulating film, when the processing time and the processing pressure are changed. FIG. 14 shows the peak distribution of the nitrogen concentration based on the results of FIG. 13. From these results, the control of the nitrogen concentration on the surface side is possible according to the processing pressure, the processing time, and Ar/N2 (flow rate ratio), and preferably, the case of No. 5 is the most suitable because it has the excellent electrical characteristic of the device.

As has been explained so far, according to the present invention, the plasma oxidation processing and the plasma nitridation processing are performed at the same time to the surface of the semiconductor substrate, and therefore the trap characteristic of the insulating film to be formed is improved. Moreover, it is possible to obtain the insulating film far exceeding the conventional one in terms of the TDDB and the leakage current.

Furthermore, when the plasma nitridation processing is further performed after the plasma oxidation and nitridation processing as described above, it is possible to control the distribution of the nitrogen in the direction of the depth, which has been difficult according to the oxynitridation processing at thermal processing of high temperature. As a result of this, it is possible to obtain the oxynitride film having the characteristic suitable for its use.

As described thus far, according to the present invention, it is possible to obtain the semiconductor substrate having the electrical characteristic and reliability which are equivalent to or greater than the thermal oxide film, even though the insulating film is formed at low temperature.

The present invention is useful in forming the insulating film of the semiconductor devices, particularly the nonvolatile memory.

What is claimed is:

1. A plasma processing method applying oxynitridation processing to a silicon substrate in a process vessel by using plasma, comprising the steps of:
    introducing an inert gas, $N_2$, and $O_2$ into the process vessel;
    making a mixed gas of the inert gas, $N_2$, and $O_2$ into a plasma by an antenna in the process vessel to form oxygen radicals and nitrogen radicals; and
    forming a silicon oxynitride film by applying oxynitridation processing to a surface of the silicon substrate by the oxygen radicals and the nitrogen radicals,
    wherein the flow rate ratio of the $O_2$ to $N_2$ is 1:4 to 1:6, and
    wherein a nitrogen concentration in the silicon oxynitride film has two peaks including a first peak near the surface of the silicon oxynitride film that is higher than a second peak near the interface between the silicon oxynitride film and the substrate.

* * * * *